United States Patent

Niemeyer

(10) Patent No.: US 9,170,244 B2
(45) Date of Patent: Oct. 27, 2015

(54) METHOD FOR THE DYNAMIC DETECTION OF LEAKAGES FOR SCR CATALYTIC CONVERTERS

(75) Inventor: Jens Niemeyer, Friedrichshafen (DE)

(73) Assignee: MTU Friedrichshafen GmbH, Friedrichshafen (DE)

( * ) Notice: Subject to any disclaimer, the term of this patent is extended or adjusted under 35 U.S.C. 154(b) by 253 days.

(21) Appl. No.: 13/985,079

(22) PCT Filed: Feb. 7, 2012

(86) PCT No.: PCT/EP2012/000559
§ 371 (c)(1),
(2), (4) Date: Oct. 10, 2013

(87) PCT Pub. No.: WO2013/041154
PCT Pub. Date: Mar. 28, 2013

(65) Prior Publication Data
US 2014/0030810 A1   Jan. 30, 2014

(30) Foreign Application Priority Data

Feb. 16, 2011   (DE) .......................... 10 2011 011 441

(51) Int. Cl.
*G01N 31/10* (2006.01)
*F01N 3/20* (2006.01)
*F01N 9/00* (2006.01)
(Continued)

(52) U.S. Cl.
CPC ............ *G01N 31/10* (2013.01); *B01D 53/9495* (2013.01); *F01N 3/208* (2013.01); *F01N 3/2066* (2013.01); *F01N 9/005* (2013.01); *F01N 11/00* (2013.01); *B01D 53/9418* (2013.01); *F01N 2550/03* (2013.01); *F01N 2560/026* (2013.01); *F01N 2570/14* (2013.01); *F01N 2610/02* (2013.01); *F01N 2900/0402* (2013.01); *F01N 2900/0408* (2013.01); *F01N 2900/0411* (2013.01); *F01N 2900/0412* (2013.01); *F01N 2900/0416* (2013.01); *F01N 2900/1402* (2013.01); *F01N 2900/1616* (2013.01); *F01N 2900/1621* (2013.01); *Y02T 10/24* (2013.01); *Y02T 10/47* (2013.01)

(58) Field of Classification Search
CPC .................................................... G01N 31/10
USPC .............. 436/37, 50, 113, 159, 181; 422/68.1
See application file for complete search history.

(56) References Cited

U.S. PATENT DOCUMENTS

| 6,868,294 | B2 | 3/2005 | Kouno et al. |
| 7,028,465 | B2 | 4/2006 | Ripper et al. |

(Continued)

FOREIGN PATENT DOCUMENTS

| DE | 19907669 C1 | 11/2000 |
| DE | 102005042490 A1 | 3/2007 |

(Continued)

OTHER PUBLICATIONS

PCT International Search Report dated Jun. 19, 2013 for PCT/EP2012/000559.

*Primary Examiner* — Arlen Soderquist
(74) *Attorney, Agent, or Firm* — Fishman Stewart Yamaguchi PLLC

(57) ABSTRACT

A method and an arrangement for dynamic breakthrough detection is proposed. The arrangement comprises at least a transfer element, at least a memory unit in which sensor characteristic curves, at least a controller and an evaluation logic are stored.

10 Claims, 3 Drawing Sheets

(51) Int. Cl.
  *F01N 11/00*   (2006.01)
  *B01D 53/94*   (2006.01)

(56) References Cited

U.S. PATENT DOCUMENTS

| | | | |
|---|---|---|---|
| 7,546,728 B2 | 6/2009 | Ripper et al. | |
| 8,061,126 B2 | 11/2011 | Gady et al. | |
| 8,341,944 B2 | 1/2013 | Walde et al. | |
| 8,393,143 B2 | 3/2013 | Walz et al. | |
| 2005/0284134 A1* | 12/2005 | Radhamohan et al. | 60/286 |
| 2007/0142975 A1* | 6/2007 | Piche | 700/286 |
| 2008/0022658 A1* | 1/2008 | Viola et al. | 60/286 |
| 2008/0250774 A1* | 10/2008 | Solbrig | 60/295 |
| 2009/0185954 A1 | 7/2009 | Qi et al. | |
| 2010/0043397 A1 | 2/2010 | Wang et al. | |
| 2010/0242454 A1 | 9/2010 | Holderbaum | |
| 2010/0281855 A1* | 11/2010 | Sun et al. | 60/286 |
| 2010/0313548 A1* | 12/2010 | Theis | 60/276 |
| 2011/0138779 A1* | 6/2011 | Neumayer | 60/274 |
| 2011/0192147 A1* | 8/2011 | Hoskin | 60/286 |
| 2011/0219747 A1* | 9/2011 | Geveci et al. | 60/274 |
| 2012/0073265 A1* | 3/2012 | Yeager et al. | 60/274 |
| 2012/0260634 A1* | 10/2012 | Devarakonda et al. | 60/274 |

FOREIGN PATENT DOCUMENTS

| | | |
|---|---|---|
| DE | 102008054952 A1 | 6/2010 |
| DE | 102008064606 A1 | 6/2010 |
| EP | 1105724 A2 | 6/2001 |
| EP | 2000641 A2 | 12/2008 |
| EP | 2180157 A2 | 4/2010 |
| EP | 2192282 A2 | 6/2010 |

* cited by examiner

METHOD FOR THE DYNAMIC DETECTION OF LEAKAGES FOR SCR CATALYTIC CONVERTERS

TECHNICAL FIELD

The present disclosure relates generally to catalytic converters used in motor vehicles.

BACKGROUND

Catalytic converters are used in motor vehicles for exhaust gas treatment to reduce harmful emissions in the exhaust gas. There are various known types of catalytic converters, such as three-way catalytic converters, unregulated oxidation catalytic converters and SCR catalytic converters.

In SCR catalytic converters, so-called selective catalytic reduction (SCR: Selective Catalytic Reduction) is used as a method for the reduction of nitrogen oxides. The chemical reaction in an SCR catalytic converter is selective, thus the nitrogen oxide (NO, $NO_2$) is reduced, while undesired side reactions, such as oxidation of the sulfur to sulfur dioxide, are largely suppressed.

In internal combustion engines used in motor vehicles, the reduction of nitrogen oxides by the SCR method proves to be difficult because there exist varying operating conditions, which makes the dosage of reducing agents difficult.

A reducing agent is dosed for the operation of SCR catalytic converters, whereby a $NO_x$ sensor value is controlled after SCR. The $NO_x$ sensor has a cross-sensitivity to $NH_3$. If overdosing takes place in the system, then a so-called $NH_3$ slip is the result after the SCR reaction, or increased $NO_x$ emissions arise again after the SCR if a slip catalyst is used in the system after the SCR.

The NO sensor therefore presents ambiguity in a characteristic curve. Therefore, it cannot be predictably differentiated whether the dosage is too low and whether $NO_x$ emissions are present, or whether the dosage is too high and a $NH_3$ slip or increased $NO_x$ emission is present due to $NH_3$ conversion in the slip catalyst.

The problem described does not occur when only low $NO_x$ conversion rates are required through the SCR catalytic converter. Then the conversion in the system is far from the maximum possible conversion with the so-called slip limit. However, high conversion rates must be achieved for fuel-saving engine tuning and efficient utilization of the catalytic converter.

Another way to resolve the ambiguity of the characteristic curve is to introduce artificially small changes in the dosage quantity of the reducing agent. By appropriate evaluation of the $NO_x$ value after the SCR, the presence of an $NH_3$ slip can be detected. Such an approach is described in DE 10 2009 012 092 A1.

Such an evaluation, however, only works when the system is in a steady state; thus the existence of an $NH_3$ slip is only detected after a certain delay.

SUMMARY

In the present disclosure, a method for dynamic breakthrough detection is proposed, whereby an $NH_3$ slip or increased $NO_x$ emission can be identified quickly during operation through $NH_3$ conversion in the slip catalyst. In the proposed method, it is not necessary to wait for a stationary operating point of the SCR catalytic converter. It is also not necessary to carry out a special variation of the dosage quantity of the reducing agent for the method, while the regular operation of the SCR control system remains in a steady state.

In the exemplary method for dynamic detection of breakthrough or $NH_3$ slip of an SCR catalytic converter operating in an exhaust gas after-treatment system, the dosage rate of a reducing agent that is added to the exhaust gas stream upstream of the SCR catalytic converter is calculated by using a model of the dynamic behavior of the SCR catalytic converter, in which parameters are used that are dependent on one or more operating parameters of the SCR catalytic converter, e.g. temperature or exhaust gas mass flow, for at least one linear sensor characteristic curve which maps the region of normal operation and at least one linear sensor characteristic curve which maps the region of the breakthrough or $NH_3$ slip, or, respectively, an expected value of the conversion rate is determined. This expected value is compared with a real conversion rate value determined by an NO sensor arranged downstream of the SCR catalytic converter. A control variable is calculated for each of the characteristic curves for adjustment of the actual conversion rate to the expected value in each case, and the characteristic curve is selected for which the smallest control value was calculated. If this is a characteristic curve that maps the region of the breakthrough or $NH_3$ slip, this indicates a breakthrough or $NH_3$ slip, and this information can be fed back to the control of the dosage of the reducing agent.

The proposed method can be used both in exhaust gas treatment systems without an additional slip catalyst for the oxidation of $NH_3$ after the SCR catalytic converter, as well as in systems that have such a slip catalyst.

In addition to the detection of an $NH_3$ slip, the maximum achievable conversion rate can also be determined at the operating point of the SCR catalytic converter under consideration. The maximum conversion rate of the SCR catalytic converter so determined can also be used to monitor the SCR catalytic converter, e.g. for the monitoring of catalyst aging.

Furthermore, an arrangement suitable for implementing the method is also proposed herein. The arrangement comprises at least a transfer element, at least a memory unit in which the sensor characteristics are stored, at least a controller and an evaluation logic. A dynamic model can be used as the transfer element, comprising, for example, a $PT_1$ element, a $PT_1$ element with dead time (Tt) or a $PT_2$ element. A PI controller, an adaptive controller or an adaptive PI controller may be used, for example, as a controller.

DETAILED DESCRIPTION OF THE DRAWINGS

Further advantages and embodiments of the disclosure will be apparent from the description and the accompanying drawings.

It is understood that the features mentioned above and those still to be explained may also be used not only in each of the given combinations, but in other combinations or alone while remaining within the scope of the present disclosure.

The disclosure is schematically illustrated by means of embodiments in the drawings and will be described below with reference to the drawings.

DETAILED DESCRIPTION

Figure 1:
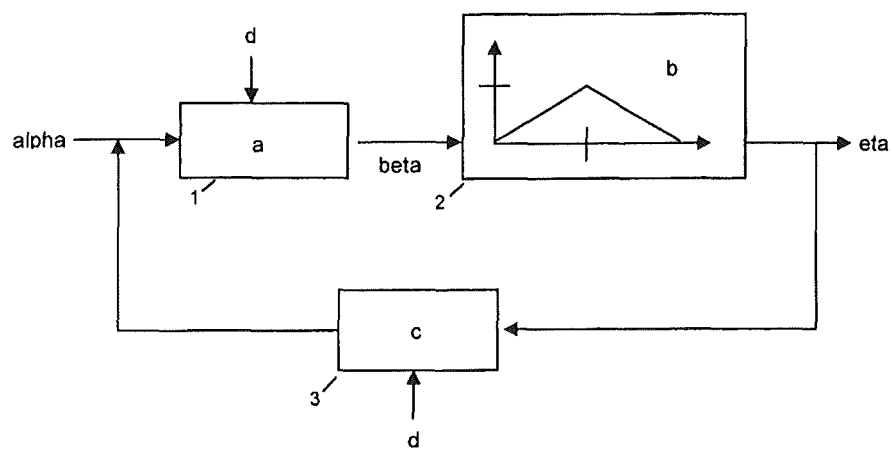
FIG. 1 shows an abstract representation of the dynamic behavior of an SCR catalyst.

FIG. 1 shows an abstract representation of the dynamic behavior of an SCR catalytic converter, whereby a transfer element 1 is implemented in this case as a $PT_1$ element with dead time (Tt), adaptively with parameters depending on a catalyst temperature. The input quantity is the alpha dosage rate; the output quantity is the eta conversion rate. Sensor behavior is shown as a characteristic curve with a break point at a maximum conversion, whereby the cross-sensitivity of the sensor to $NH_3$ is reflected in a negative gradient of the characteristic curve in the breakthrough region. The parameters can be determined by step attempts in order to determine a target conversion or from model calculations. The sensor characteristic curve is stored in a memory unit 2. The control of the dosage rate is affected via a controller 3; in the case illustrated, this is an adaptive PI controller.

Figure 2:
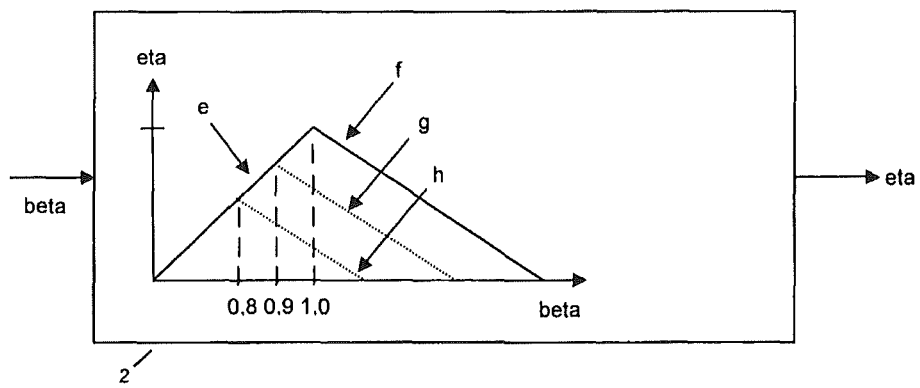
FIG. 2 shows examples of sensor characteristic curves for various maximum conversion rates.

FIG. 2 shows sensor characteristic curves for various maximum conversion rates. The curves are each composed of two sub-lines, a sub-line with a positive slope for normal operation and a sub-line with a negative slope for the breakthrough region. The changeover point between the normal operation and the breakthrough region, identified as the maximum of the characteristic curve, is dependent on the respective maximum conversion rate of the catalyst. Curves for maximum reaction rates of 0.8, 0.9 and 1.0 are shown in FIG. 2.

All possible normal operation and breakthrough region variations with various maximum conversion rates are combined into a general model for the described method. The general model is subdivided into corresponding linear sub-models, each composed of the time behavior ($PT_1$, $PT_1$ and dead time, or $PT_2$) and a linear characteristic curve, while the sub-models are transformed into linear control models. An associated observer structure is designed for each sub-model, and a dosage quantity is determined based on the corresponding model calculation, which leads to exact matching of the model and reality. A PI observer is used in order to reach steady-state accuracy. The observer control variables obtained for the different linear sub-models are compared. The model with the lowest observer control variable best matches the real behavior of the system. This model is selected and provides information on whether a breakthrough is present and what the maximum conversion rate of the real system is. In the selection, it should be noted that each model, whose maximum conversion rate corresponds to the current actual conversion rate, is excluded, because a distinction between normal operation and breakthrough operation is not possible with the current actual conversion rate.

Figure 3:
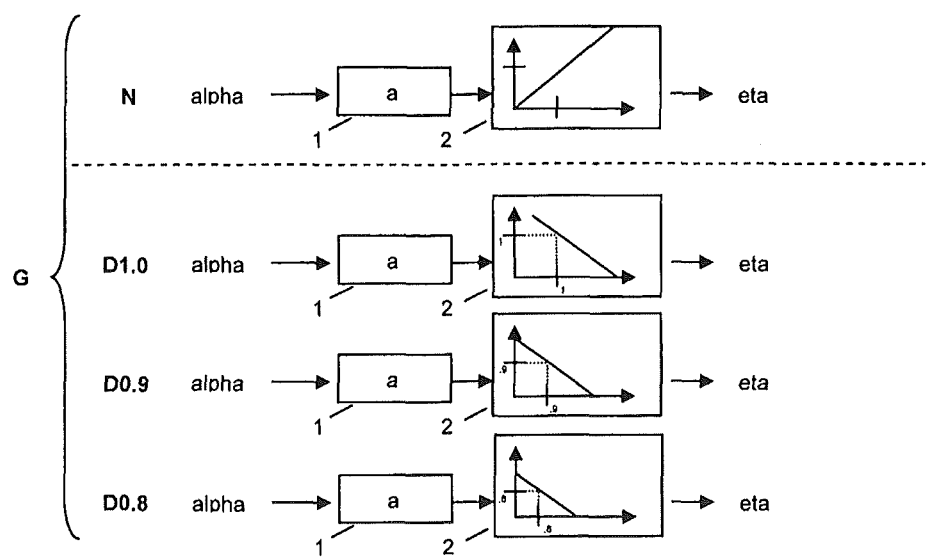
FIG. 3 shows an example of a general model of the dynamic behavior of an SCR catalytic converter subdivided into sub-models.

FIG. 3 shows an example of a general model transformed into linear sub-models. It includes a sub-model for normal operation and three sub-models for the breakthrough, each with different maximum conversion rates, respectively shown with transfer element 1 and sensor characteristic curves stored in the memory unit 2. The output equations for the sub-models in the breakthrough region is a straight line which does not pass through the origin. The slope of the line results from the cross-sensitivity of the $NO_x$ sensor to $NH_3$ and its y-axis intercept from its slope and the maximum conversion.

Figure 4:
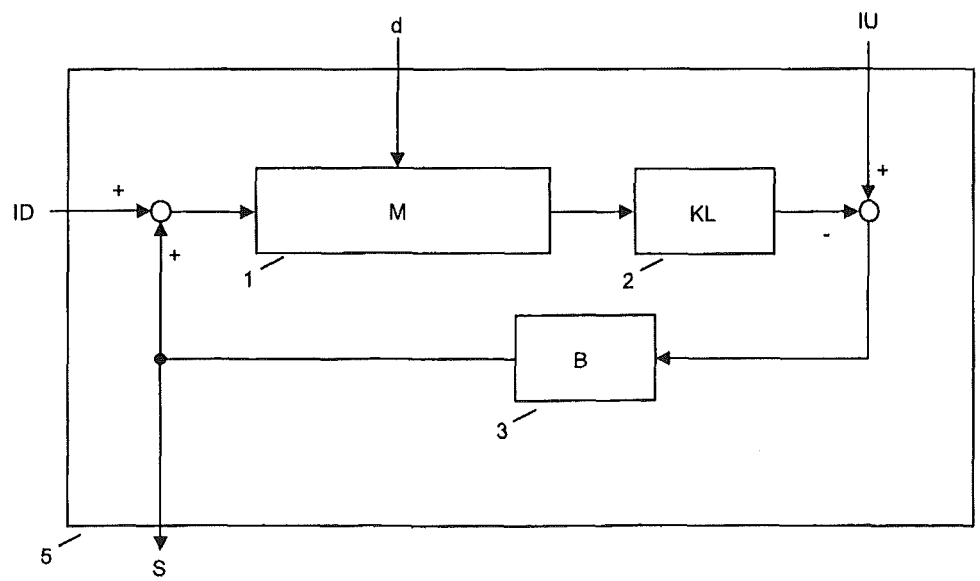
FIG. 4 shows schematically an example of an observer structure used in the described method.
Figure 5:
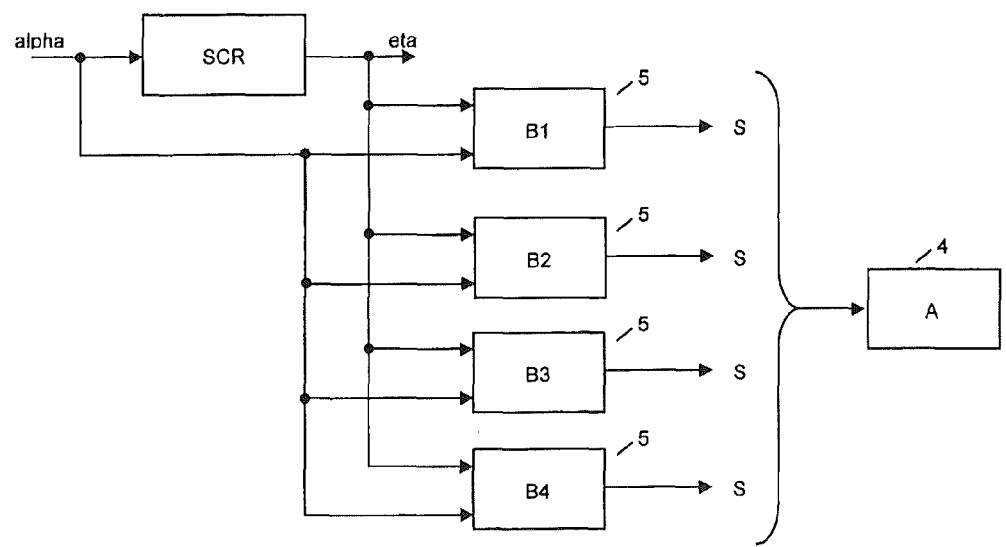
FIG. 5 shows schematically an embodiment of the described method.

FIG. 4 shows an observer structure 5 used in the described method, and comprising a transfer element 1, a memory unit 2 with sensor characteristic curves and a controller 3. The sub-model observed is compared to the real conversion, whereby the observer 5 of the control corresponds to the real conversion with a PI controller for steady-state accuracy, while the control action of the observer 5 establishes the correspondence between the actual conversion and the conversion calculated in the sub-model. FIG. 5 shows schematically an embodiment of the described method. The control variables of the observer 5 calculated in the sub-model used are compared through an evaluation logic 4. The sub-model with the smallest observer control variable is the one that shows the best correspondence with the real system. This sub-model is selected and it is thereby determined whether a breakthrough is present and what the maximum conversion rate of the SCR catalytic converter is.

The system so described makes it possible to detect a breakthrough of the SCR catalytic converter or the $NH_3$ slip, and to determine the maximum conversion rate of the SCR catalytic converter without an artificial excitation of the system being required. The automatic excitations resulting from the operation of the system with a controller are sufficient. The method only requires low computational effort, as only simple linear models and PI controllers need to be calculated, while no complex model calculations are required.

The invention claimed is:

1. A method for monitoring an SCR catalyst operated in an exhaust gas after-treatment system, comprising:
   a. determining at least one linear sensor characteristic curve from a dosage rate of a reducing agent added to exhaust gas upstream of an SCR catalytic converter, based on a model of dynamic behavior of the SCR catalytic converter, wherein the at least one linear sensor characteristic curve maps a region of normal operation, and wherein the at least one linear sensor characteristic curve maps a region of breakthrough or $NH_3$ slip, from which an expected value of a conversion rate is determined;
   b. comparing the expected value with a real conversion rate determined from a value determined by an $NO_x$ sensor arranged downstream of the SCR catalytic converter;
   c. calculating in each case, a control variable for an adjustment of the real conversion rate to the expected value for each characteristic curve; and
   d. selecting the characteristic curve for which a lowest control value was calculated.

2. A method according to claim 1, whereby the monitoring includes a dynamic detection of a catalytic converter breakthrough.

3. A method according to claim 1, whereby the monitoring includes the a determination of the maximum conversion rate of the catalytic converter.

4. A method according to claim 1, whereby a plurality of various characteristic curves represents the region of the breakthrough.

5. A method according to claim 4, whereby the various characteristic curves correspond to various maximum conversion rates.

6. A method according to claim 1, whereby parameters used in the model of the dynamic behavior of the SCR catalytic converter are dependent on one or more operating parameter(s) of the SCR catalytic converter.

7. An arrangement, for implementing the method according to claim 1, comprising at least a transfer element, at least a memory unit in which the sensor characteristic curve maps are stored, at least a controller and an evaluation logic.

8. The arrangement according to claim 7, whereby the at least one transfer element comprises a dynamic model.

9. The arrangement according to claim 7, whereby the at least one controller comprises a PI controller.

10. The arrangement according to claim 7, whereby the at least one controller comprises an adaptive controller.

\* \* \* \* \*